United States Patent [19]

van Andel

[11] Patent Number: Plant 5,589

[45] Date of Patent: Dec. 3, 1985

[54] CARNATION NAMED MUFUGO

[75] Inventor: Jacob van Andel, Aalsmeer, Netherlands

[73] Assignee: B. V. Handelskwekerij/M. C. van Staaveren, Aalsmeer, Netherlands

[21] Appl. No.: 556,458

[22] Filed: Nov. 30, 1983

[51] Int. Cl.[4] ..... A01H 5/00

[52] U.S. Cl. ..... Plt./70

[58] Field of Search ..... Plt./70–72

*Primary Examiner*—Robert E. Bagwill

*Attorney, Agent, or Firm*—Chas. W. Rummler

[57] ABSTRACT

A new variety of miniature carnation characterized by its rapid and continuous production of small red-purple blooms with a larger number than normal of flowers appearing on each flower stem and its tall, strong and upright growth habit.

1 Drawing Figure

BACKGROUND OF THE NEW PLANT

This new variety of miniature carnation plant originated as a seedling of unknown parentage growing among a group of carnation plants maintained in greenhouse for breeding purposes at Aalsmeer, The Netherlands, this particular plant having been selected by me for propagation because of its profuse production of small red-purple blooms with more than usual appearing on each flowering stem. I propagated this new plant by means of cuttings with very favorable results, which prompted me to continue propagation through several successive generations to observe its growth habits and the stability of its novel and distinctive features and I thereby found that the distinctive characteristics of the plant were maintained true from generation to generation and appeared to be firmly fixed.

DESCRIPTION OF THE DRAWING

This new variety of carnation plant is illustrated by the accompanying photographic drawing which shows a plurality of flower stems bearing buds in various stages of opening and blooms from newly opened to fully mature state, several of the blooms being hand painted to show the specified colors as nearly true as is reasonably possible.

DESCRIPTION OF THE NEW PLANT

The following is a detailed description of my new variety of miniature carnation plant as observed on greenhouse plants early in the Summer of 1983, the color designations being according to The R.H.S. Colour Chart published by The Royal Horticultural Society of London, England.

THE PLANT

Origin: Seedling.
Parentage:
- *Seed parent.*—Unknown.
- *Pollen parent.*—Unknown.

Classification:
- *Botanic.*—*Dianthus caryophyllus* Hybrid.
- *Commercial.*—Miniature carnation.

Form: Bush.
Height: Varies depending upon season.
Growth: Strong and upright with normal branching.
Foliage:

- *Quantity.*—Moderate.
- *Number of leaves.*—Depends on season.
- *Size of leaf.*—Medium.
- *Shape.*—Oblong.
- *Texture.*—Smooth.
- *Color.*—Upper side — Grey/Green. Under side — Grey/Green.

THE BUD

Form: Pointed ovoid becoming cylindrical as sepals divide.
Size: Small.
- *Diameter.*—About 8 mm.
- *Length.*—About 30 mm.

Opening rate: Moderate.
Color:
- *When sepals first divide.*—Red, becoming Red-Purple when petals begin to unfurl.

Sepals:
- *Shape.*—Pointed oblong.
- *Character.*—Sepals stand up when flowers open.
- *Color.*—Inside — Grey/Green. Outside — Grey/-Green.

Calyx:
- *Shape.*—Funnel-shaped
- *Size.*—Long.
- *Aspect.*—Smooth.
- *Splitting.*—The calyx rarely splits.

Flower stem:
- *Character.*—Long and rigid.
- *Color.*—Grey/Green.

THE FLOWER

Blooming habit: Profuse and continuous.
Size of bloom: Small.
- *Diameter.*—About 40 mm.
- *Depth.*—About 20 mm.

Shape:
- *When bloom first opens.*—High centered.
- *When bloom matures.*—Petals fully open and spread.

Petalage:
- *Number of petals.*—Approximately 30.
- *Arrangement.*—Overlapping.
- *Form.*—Fan-shaped with deeply serated margins.
- *Texture.*—Soft.
- *Appearance.*—Shiny.

*Color.*—All petals: Top side: Body — R.H.S. 74A. Base — Pale Green. Reverse side — R.H.S. 74A. Colors are the same for all seasons.

Flower stem:

*Length.*—Various depending on season.

*Character.*—Strong and upright.

*Color.*—Grey/Green.

Fragrance: Weak.

Persistence: Petals hang on and dry.

Disease resistance: The flowers are less susceptible to *Fusarium oxysporum* as observed in the Aslsmeer district of The Netherlands.

Lasting quality:

*On plant.*—Approximately 15 days.

*As cut flower.*—Approximately 10 days.

REPRODUCTIVE ORGANS

Stamens: Moderate in number.

*Anthers.*—Size: Medium. Color: Yellow.

Filaments.—Color: White.

*Pollen.*—If present, color is yellow.

Pistils:

*Number.*—One.

*Style.*—Length: About 15 mm. Color: White.

*Stigma.*—Color: White and violet.

This particular miniature carnation has the advantage of a very fast and profuse production of quite small flowers with considerably more appearing on each flower than would ordinarily occur. Also, the blooms of this plant are less susceptible to *fusarium oxysporum* than would be normal.

I claim:

1. The new and distinct variety of miniature carnation plant, substantially as herein shown and described, characterized in particular by its rapid and profuse production of small red-purple flowers and the large number of flowers appearing on each flowering stem.

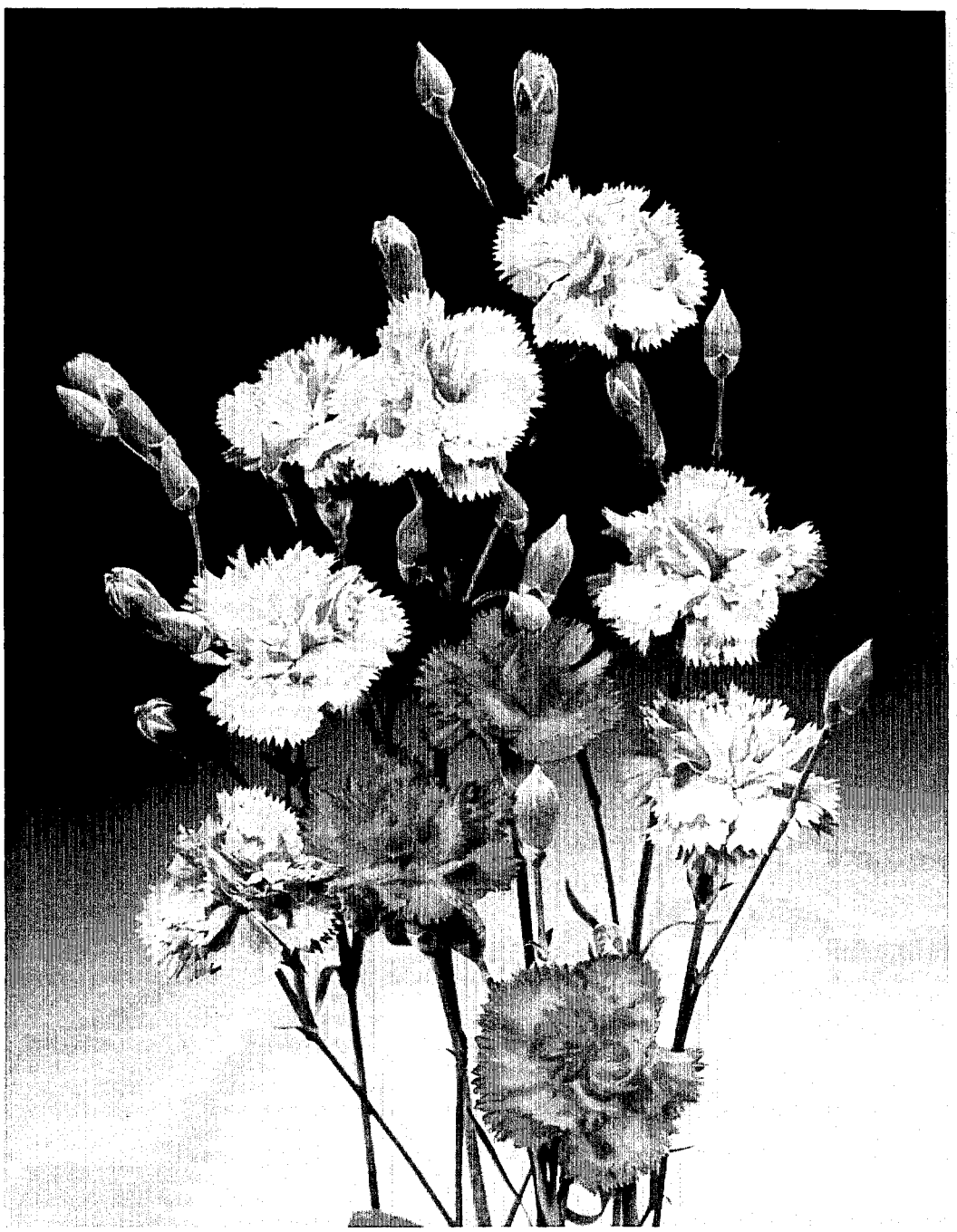

* * * * *